United States Patent [19]
Magnani

[11] Patent Number: 5,965,457
[45] Date of Patent: Oct. 12, 1999

[54] METHODS OF SCREENING FOR A CANDIDATE COMPOUND ABLE TO BIND TO CD34+ CELLS

[76] Inventor: John L. Magnani, 13713 Woodlark Dr., Rockville, Md. 20853

[21] Appl. No.: 08/471,719

[22] Filed: Jun. 6, 1995

[51] Int. Cl.$^6$ .................................................. G01N 33/543
[52] U.S. Cl. ........................ 436/518; 435/7.1; 435/7.2; 435/7.21; 435/7.5; 435/7.9; 435/7.92; 435/7.94; 436/501; 436/524; 436/525; 436/526; 436/527; 436/528; 436/529; 436/531
[58] Field of Search ............................. 435/7.1, 7.2, 7.9, 435/7.21, 7.92, 7.5, 7.94, 7.7, 7.71, 7.72, 240.1, 240.243; 436/501, 518, 524, 525, 526, 527, 528, 529, 531

[56] References Cited

U.S. PATENT DOCUMENTS

| | | | |
|---|---|---|---|
| 4,714,680 | 12/1987 | Civin | 435/240.25 |
| 5,032,519 | 7/1991 | Paulson et al. | 435/193 |
| 5,081,030 | 1/1992 | Civin | 435/240.2 |
| 5,215,927 | 6/1993 | Berenson et al. | 436/541 |
| 5,225,353 | 7/1993 | Berenson et al. | 436/541 |
| 5,262,334 | 11/1993 | Berenson et al. | 436/541 |

OTHER PUBLICATIONS

Kessler, "Epitope diversity and structure of the CD34 (p. 115) hematopoietic progenitor cell antigen," Naval Research Institute Federation Proceedings vol. 46, No. 4 1987, 6109.

Andrews et al., "Monoclonal Antibody 12–8 Recognizes a 115–kd Molecule Present on Both Unipotent and Multipotent Hematopoietic Colony–Forming Cells and Their Precursors," *Blood* 67 (3): 842–845, 1986.

Crocker et al., "Sialoadhesin Binds Preferentially to Cells of the Granulocytic Lineage," *J. Clin. Invest.* 95: 635–643, 1995.

Crocker et al., "Sialoadhesin, a macrophage sialic acid binding receptor for haemopoietic cells with 17 immunoglobulin–like domains," *EMBO Journal* 13: 4490–4503, 1994.

de Vries and van den Eijnden, "Biosynthesis of Sialyl–Oligomeric–Lewis$^X$ and VIM–2 Epitopes: Site Specificity of Human Milk Fucosyltransferase," *Biochemistry* 33: 9937–9944, 1994.

Srivastava and Hindsgaul, "Synthesis of Polylactosamine Oligomers By Disaccharide Polymerization," *J. Carbohydrate Chemistry* 10 (5): 927–933, 1991.

Sutherland et al., "CD34 Antigen: Molecular Features and Potential Clinical Applications," *Stem Cells* 11 (suppl. 3): 50–57, 1993.

Sutherland et al., "Cleavage of the Cell–Surface O–Sialoglycoproteins CD34, CD43, CD44, and CD45 By a Novel Glycoprotease From *Pasteurella haemolytica*," Journal of Immunology 148 (5): 1458–1464, 1992.

Sutherland et al., "Differential Sensitivity of CD34 Epitopes to Cleavage by *Pasteurella haemolytica* Glycoprotease: Implications for Purification of CD34–positive Progenitor Cells," *Exp. Hematol.* 20: 590–599, 1992.

Tomalia, D., "Dendrimer Molecules," *Scientific American* (May): 62–66, 1995.

*Primary Examiner*—Christopher L. Chin
*Attorney, Agent, or Firm*—Seed and Berry LLP

[57] ABSTRACT

Compounds and methods are provided for use in purification of CD34+ cells and specific surface antigens thereof. The present invention discloses methods for releasing CD34+ cells, as well as compounds having a carbohydrate epitope of the CD34 surface antigen, from an affinity matrix, using carbohydrates having the structure:

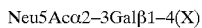

Neu5Acα2–3Galβ1–4(X)

wherein (X) is GlcNAc, or a monosaccharide or a cyclohexane derivative that is structurally similar to GlcNAc.

10 Claims, 5 Drawing Sheets

METHODS OF SCREENING FOR A CANDIDATE COMPOUND ABLE TO BIND TO CD34+ CELLS

TECHNICAL FIELD

The present invention relates generally to methods and compositions for the purification of CD34+ cells and specific antigens. The invention is more particularly directed to methods and compositions useful for releasing CD34+ cells, or compounds having a specific carbohydrate epitope of the CD34 surface antigen, from a binding partner, which may be immobilized on an affinity matrix. The invention is also directed to methods for identifying compounds that bind to CD34+ cells.

BACKGROUND OF THE INVENTION

Bone marrow transplantation is a critical procedure for treatment of a variety of diseases, such as leukemia, cancer and certain genetic diseases. The transplantation process involves the repopulation of a patient's bone marrow stem cells following ablative treatment, such as chemotherapy or radiation therapy. Serious problems can result, however, from transplantation of impure preparations of bone marrow stem cells. In allogenic transplantations (i.e., transplantation with bone marrow cells from a genetically different donor), preparations that contain other types of cells, particularly T lymphocytes, can induce graft vs. host disease in the patient. This problem can be prevented through the use of autologous transplantation (i.e., transplantation with the patient's own marrow). However, preparations of the patient's marrow cells may be contaminated with diseased cells, resulting in ineffective treatment.

To alleviate the problems associated with contaminated preparations, a variety of methods for purification of stem cells are currently employed. Such methods often employ affinity procedures to selectively remove specific contaminating cells from a stem cell preparation. For example, monoclonal antibodies to a variety of contaminating cells types, such as T cells and cancer cells, have been employed. Because of the wide variety of contaminating cells, however, purification procedures based on selective removal of individual cell types are often incomplete. Such procedures also may involve many steps, rendering the purification process extremely costly and inefficient.

The purification process may also use affinity procedures to selectively isolate the desired cells. For example, monoclonal antibodies have been employed that selectively recognize an epitope on the CD34 antigen. Such antibodies may be used to isolate cells expressing the CD34 antigen, which include nearly all stem cells and early stage committed B lymphoid cells. These antibodies do not bind mature B cells, T cells, NK cells, monocytes, granulocytes, platelets or erythrocytes. Accordingly, the use of such specific antibodies can provide a more effective, and lower cost, method of purifying bone marrow stem cells.

However, while CD34-specific affinity matrices containing immobilized antibodies have significant advantages in the capture of cells expressing the CD34 antigen, the release of CD34+ cells from such affinity matrices has been problematic. Release is commonly effected by physically shearing the cells from the matrix. This procedure can cause cell damage, and can leave antibody bound to the released cells. Alternatively, enzymatic cleavage may be employed, to degrade the antibody to which the CD34 antigen is bound. This procedure has the advantage of decreasing cell damage and removing bound antibody from the cells. However, the enzymes employed could damage other cell surface proteins, and are inconvenient to use because of the necessity to monitor cell viability after treatment.

Accordingly, there is a need in the art for a method for releasing CD34+ cells from affinity matrices that overcomes the disadvantages encountered with existing methods. The present invention fulfills this need and provides further related advantages.

SUMMARY OF THE INVENTION

Briefly stated, this invention provides methods and compositions for the release of CD34+ cells, and specific surface antigens thereof, from affinity matrices. In one aspect of the invention, methods are provided for releasing a CD34+ cell from a CD34+-binding partner complex, comprising contacting a complex of a CD34+ cell and a binding partner with a carbohydrate having the structure NeuSAcα2–3Galβ1–4 (X), wherein (X) is GlcNAc or a structurally similar analog thereof. In a preferred embodiment, the carbohydrate has the structure NeuSAcα2–3(Galβ1–4GlcNAcβ1–3)$_n$, wherein n is an integer from 1 to 50.

In a related aspect of the invention, methods are provided for purifying CD34+ cells, comprising the steps of: (a) contacting a biological sample containing CD34+ cells with a binding partner, to form a CD34+-binding partner complex; (b) separating the CD34+-binding partner complex from unbound biological sample; (c) contacting the CD34+-binding partner complex with a carbohydrate having the structure NeuSAcα2–3Galβ1–4(X), wherein (X) is GlcNAc or a structurally similar analog thereof; and (d) collecting the CD34+ cells.

In yet another aspect of the present invention, methods are provided for releasing a molecule that binds monoclonal antibody 12.8 from a binding partner, comprising contacting a complex of the molecule and a binding partner with a carbohydrate having the following structure NeuSAcα2–3Galβ1–4(X), wherein (X) is GlcNAc or a structurally similar analog thereof.

In a related aspect, this invention provides methods for purifying a molecule that binds monoclonal antibody 12.8, comprising the steps of: (a) contacting a sample containing a molecule that binds monoclonal antibody 12.8 with a binding partner, to form a complex; (b) separating the complex from unbound sample; (c) contacting the complex with a carbohydrate having the structure NeuSAcα2–3Galβ1–4(X), wherein (X) is GlcNAc or a structurally similar analog thereof; and (d) collecting the molecule.

In still another aspect of this invention, methods are provided for screening for a candidate compound able to bind to CD34+ cells, comprising the steps of: (a) contacting a candidate compound with a carbohydrate having the structure NeuSAcα2–3Galβ1–4(X), wherein (X) is GlcNAc or a structurally similar analog thereof; and (b) detecting candidate compound bound to the carbohydrate, thereby identifying a candidate compound that binds to CD34+ cells.

These and other aspects of the present invention will become apparent upon reference to the following detailed description. All references disclosed herein are hereby incorporated by reference in their entirety as if each was incorporated individually.

DETAILED DESCRIPTION OF THE INVENTION

Figure 1:
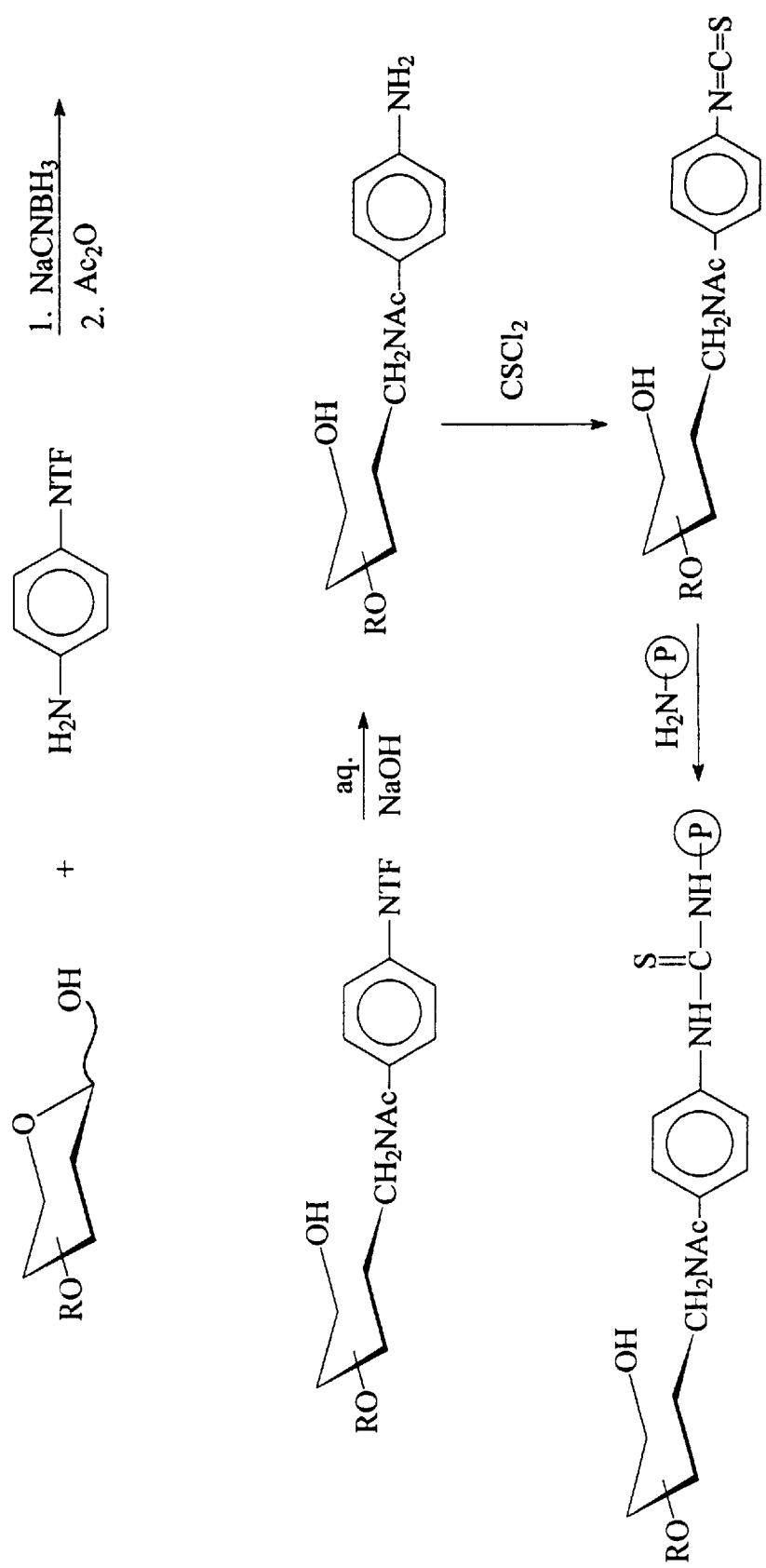
FIG. 1 depicts the coupling of oligosaccharides to amine containing carrier groups, such as serum albumin.

As noted above, the present invention is generally directed to methods and compositions for releasing CD34$^+$ cells, or molecules having a specific carbohydrate epitope of the CD34 surface antigen, from a binding partner. Such methods are useful, for example, in purifying CD34$^+$ cells. The present invention further discloses methods for identifying compounds that bind to CD34$^+$ cells.

Prior to setting forth the invention in detail, it may be helpful to an understanding thereof to provide definitions of certain terms to be used herein. A "binding partner," in the context of this invention, is any agent, such as a compound or a cell, that binds to 3'-sialyllactose (3'SL), when that saccharide is coupled to serum albumin (e.g., human or bovine serum albumin) by way of aminophenylene diamine (APD) or 2-(4-aminophenyl)ethylamine (APEA). Binding partners, within this invention, also bind to the defucosylated sialyl Le$^x$ epitope (with or without a carrier group), and compete with monoclonal antibody 12.8 (mAb12.8) for binding to CD34$^+$ cells. In other words, binding partners contain a binding site that is functionally equivalent to the antigen binding site on mAb12.8 for CD34$^+$ cells.

As used herein, the term "binding" refers to a noncovalent association between two separate molecules (each of which may be free (i.e., in solution) or present on the surface of a cell or a solid support), such that a "complex" is formed. Such a complex may be free or immobilized (either covalently or noncovalently) on a support material. The ability of one molecule to bind to another molecule may generally be evaluated by determining a binding constant for the formation of the complex. The binding constant is the value obtained when the concentration of the complex is divided by the product of the component concentrations. In general, two compounds are said to "bind" in the context of the present invention when the binding constant for complex formation exceeds about 10$^2$ L/mol.

The binding constant may be determined using methods well known to those of ordinary skill in the art. For example, the binding constant for the formation of a complex between a relatively small carbohydrate and a macromolecule binding partner may be determined using equilibrium dialysis. Briefly, two chambers of known volume are separated by a dialysis membrane that allows transfer of the small molecular weight carbohydrate, but not the macromolecule binding partner (e.g., an antibody). The carbohydrate is labeled with a reporter group, such as tritium, and is added to the solution in chamber 1, while the binding partner is placed in the solution in chamber 2. The carbohydrate molecules are then allowed to diffuse into chamber 2 until transfer of the carbohydrate reaches equilibrium (generally about 1 to 3 days). The binding constant may then be determined by measuring the amount of carbohydrate in each chamber (which may be readily determined using the reporter group) and using equation I:

$$K = \frac{[CB]}{[C][B]} \quad \text{I}$$

where [C] is the concentration of uncomplexed carbohydrate, [B] is the concentration of uncomplexed binding partner and [CB] is the concentration of complex. Since [C] is the concentration of carbohydrate in chamber 1 (i.e., [C$_1$]); [B] is difference between the original concentration of binding partner (i.e., [B$_0$]) and [CB]; and [CB] is the difference between the concentration of carbohydrate in chamber 2 and the concentration of carbohydrate in chamber 1 (i.e., [C$_2$]–[C$_1$]), equation I may be rewritten in measurable terms as equation II:

$$K = \frac{[C_2] - [C_1]}{[C_1]([B_i] - ([C_2] - [C_1]))} \quad \text{II}$$

Any agent (e.g., a cell or a molecule) that satisfies the above requirements may be a binding partner. In a preferred embodiment, the binding partner is an antibody, or a binding fragment thereof. More preferably, the binding partner is mAb12.8.

As used herein, a compound is said to "compete" with mAb12.8 for binding to CD34$^+$ cells if it is able to release CD34$^+$ cells that have been immobilized on a CEPRATE LC avidin column (CellPro, Inc., Bothell, Wash.) according to the manufacturer's instructions. More specifically, a compound that competes with mAb12.8 will, at a concentration of 10 mg/mL, elute at least 10% of the CD34$^+$ cells bound to the column after a sample containing at least 10$^8$ CD34$^+$ cells has been applied to the column.

In the methods of this invention, release of a cell or molecule from a binding partner is generally achieved using a carbohydrate having the following structure:

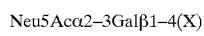

wherein (X) is GlcNAc, or a structurally similar analog thereof. Such carbohydrates include all molecules that contain the recited structure. Additional monosaccharide or non-saccharide moieties, such as carrier groups to aid in purification, detection or immobilization of the carbohydrate, may be present in a carbohydrate having the above structure.

A "structurally similar analog" of GlcNAc is any compound (which may be a monosaccharide or a non-saccharide moiety such as a cyclohexane derivative) that has a three dimensional structure similar to that of GlcNAc when used in the (X) position of the above structure. For example, it has been found in the present invention that the ring structure of glucose in the (X) position opens when linked via APD or APEA to serum albumin, rendering the glucose residue structurally similar to GlcNAc. In general, structurally similar analogs may be identified by computer modeling. Preferred carbohydrates for use in the methods of this invention include carbohydrates having the structures: (1) Neu5Acα2–3Galβ1–4(Glc)-APD-HSA (3'SL-HSA); (2) Neu5Acα2–3Galβ1–4GlcNAcβ1–3Galβ1–4Glc (defucosylated SLe$^x$); and (3) Neu5Acα2–3 (Galβ1–4GlcNAcβ1–3)$_n$, wherein n is an integer generally from 1 to 50, typically from 1 to 20 and preferably from 1 to 10.

The carbohydrates of this invention may generally be prepared from commercially available materials, using methods that will be apparent to those of ordinary skill in the art. For example, 3'SL-HSA may be prepared by coupling 3'sialyllactose to a carrier, by any of a variety of means. Defucosylated SLe$^x$ may be prepared by treating SLe$^x$ with $\alpha$1–3, 4 fucosidase. Polylactosamine chains of varying lengths may generally be prepared according to the method of Srivastava et al., *J. Carbohydrate Chem.* 10:927–933 (1991), and joined to 3'sialyllactose according to the method of De Vries and van den Eijnden, *Biochem.* 33:9937–9944 (1994).

Within the scope of this invention, any of a variety of saccharide or non-saccharide groups may be linked to the above carbohydrate structures. For example, a carrier group such as serum albumin (e.g., human or bovine), egg albumin, polylysine, a polyamidoamine, a peptide, an immunogenic protein, an antibody, polystyrene, polyacrylamide, a lipid, ceramide, biotin or a dendrimer (see Tomalia, *Scientific American* (May, 1995) at 62–66) may be covalently attached. In a preferred embodiment, the carrier group is multivalent (i.e., is able to simultaneously bind to more than one of the above carbohydrate molecules).

A carrier group may be covalently attached by any method known to those of ordinary skill in the art. In one such method, a linker such as 2-(4-aminophenyl)ethylamine (APEA) or p-trifluoroacetamidoaniline (which may be synthesized from p-nitroaniline and trifluoroacetic anhydride, followed by reductive hydrogenation) may be used. Such linkers react with the reducing end of the carbohydrate by reductive amination, and may be converted to an isothiocyanate derivative by reacting with thiophosgen. This compound is highly reactive with amines, and will couple to compounds such as proteins, phosphatidyl ethanolamine and amino groups in dendrimers and peptides. The use of such linkers has the advantages of simplicity, stability, high yield and compatibility with sialyloligosaccharides. However, the above description is provided solely for exemplary purposes, and other linking methods will be readily apparent to those in the art.

In one aspect of the present invention, methods are provided for releasing a CD34$^+$ cell from a complex that it has formed with a binding partner. A CD34$^+$ cell may generally be released from a complex with any of the binding partners discussed above by contacting the complex with a carbohydrate containing a Neu5Ac$\alpha$2–3Gal moiety joined via a $\beta$1–4 linkage to a GlcNAc residue, or a structurally similar analog thereof. In a preferred embodiment, the complex from which the CD34$^+$ cell is released is immobilized on a solid support. The solid support may be any suitable material known to those of ordinary skill in the art. For example, the solid support may be a bead, disc, hollow fiber, membrane or other matrix, or the well of a microtiter plate. Suitable materials for formation of a support include glass, fiberglass, latex, polyacrylamide, agarose, dextran or a plastic material such as polystyrene and polyvinylchloride. The support may also be a magnetic particle, such as those disclosed in U.S. Pat. Nos. 5,200,270; 4,452,773; 4,661,408; 4,695,393; 5,169,754; 4,018,886 and 5,320,944.

The manner in which the carbohydrate is contacted with the complex will depend upon the location of the complex. For example, complex immobilized on a chromatographic matrix may be contacted with a carbohydrate by passing a composition containing the carbohydrate over a column containing immobilized complex, thereby eluting the released CD34$^+$ cells from the column. Alternatively, complex (either free or immobilized) may be incubated with carbohydrate, and the released CD34$^+$ cells separated from the binding partner using any of a variety of techniques known to those of ordinary skill in the art, including filtration, precipitation and centrifugation. In either embodiment, the conditions under which the complex is contacted with carbohydrate should be similar to physiological conditions (e.g, pH 7.4 isotonic saline at room temperature for about 1–5 hours).

The amount of carbohydrate that should be contacted with the complex will vary, depending on the amount of complexed CD34$^+$ cells, and may be readily determined by performing parallel tests in which CD34$^+$ cells are released from a complex using different amounts of carbohydrate. In general, an amount of carbohydrate that releases at least 10%, preferably at least 40%, and more preferably at least 80%, of the complexed CD34$^+$ cells is sufficient. A suitable amount of carbohydrate generally ranges from about 1 $\mu$g/mL to 50 mg/mL, typically 10 $\mu$g/mL to 10 mg/mL.

In a related aspect of this invention, methods are provided for purifying CD34$^+$ cells. Preferably, the CD34$^+$ cells are present, prior to purification, in a biological sample. As used herein, a "biological sample" is any tissue sample or preparation of cells that contains CD34$^+$ cells. For example, a biological sample may be a blood preparation, with or without cytokine treatment. More preferably, the biological sample is human umbilical cord blood, a bone marrow isolate, a preparation of buffy coat cells, or a preparation of bone marrow or other cells expanded in vitro.

Briefly, purification of CD34$^+$ cells from a biological sample may be achieved by contacting the biological sample with an excess of binding partner over the number of CD34$^+$ cells within the sample, such that CD34$^+$ cells form complexes with binding partner. The amount of CD34$^+$ cells within a biological sample may generally be determined by, for example, FACS analysis using an antibody such as mAb12.8 that is specific for CD34$^+$ cells. Such analyses are commercially available (from, for example, CellCo, Rockville, Md.). Following complex formation, the complex may be separated from the remainder of the biological sample, and contacted with the carbohydrate to effect release of the CD34$^+$ cells, as described above.

Suitable conditions for contacting the binding partner with the biological sample are generally conditions that favor complex formation and maintain cell viability. Such conditions may be readily determined by one of ordinary skill in the art by evaluating the binding constant for complex formation at a series of different conditions. Suitable conditions include physiological conditions, such as pH 7.4 isotonic saline (e.g., 0.15M NaCl) at room temperature. It will be evident to those of ordinary skill in the art that the amount of binding partner necessary to achieve adequate complexation of the CD34$^+$ cells in a given biological sample will depend upon the concentration of CD34$^+$ cells within the sample, the binding constant for the given binding partner and the other materials present in the biological sample. In general a concentration of binding partner ranging from about 0.1 $\mu$g/mL to 10 mg/mL, and typically from about 1 $\mu$g/mL to 1 mg/mL, is sufficient.

The complex may be immobilized on a solid support to facilitate separation from the remainder of the biological sample. Any of a variety of techniques for immobilization known to those in the art, and amply described in the patent and scientific literature, may be employed. Immobilization may generally be achieved through noncovalent association, such as adsorption or affinity (typically using an immobilized compound that itself binds to the binding partner), or covalent attachment which may be a direct linkage between a component of the complex and functional groups on the support, or may be a linkage by way of a cross-linking agent).

Immobilization of a compound by adsorption may be achieved by contacting the compound, in a suitable buffer, with a solid support for a suitable amount of time. The contact time varies with temperature, but is generally between about 5 seconds and 1 day, and typically between about 10 seconds and 1 hour.

Covalent attachment of a compound to a solid support may generally be achieved by first reacting the support with a bifunctional reagent that will react with both the support and a functional group, such as a hydroxyl or amino group, on the compound. For example, a binding partner may be bound to a support having an appropriate polymer coating using benzoquinone or by condensation of an aldehyde group on the support with an amine and an active hydrogen on the binding partner (see, e.g., Pierce Immunotechnology Catalog and Handbook (1991) at A12–A13).

Immobilization by affinity is generally achieved using a support that contains an immobilized compound that binds to the complex. Such a compound may be immobilized by adsorption or covalently. The immobilized compound typically binds to one component of the complex; preferably the immobilized compound binds to the binding partner.

In one embodiment, one component of the complex, preferably the binding partner, is immobilized on the support prior to formation of the complex. In such cases, the complex itself is immobilized as a result of the immobilization of one of the components. In another embodiment, the complex is formed prior to immobilization by affinity. For example, a complex in which the binding partner contains a biotin carrier group (or in which the binding partner binds to a second molecule that contains a biotin group) may be immobilized after formation by binding to an avidin-coated support (see, e.g., U.S. Pat. Nos. 5,215,927; 5,225,353 and 5,262,334)

Once a complex is formed, and preferably immobilized, the complex is separated from the remainder of the biological sample. This separation may be achieved using any of a variety of techniques known to those of ordinary skill in the art such as, for example, filtration or chromatography. In general, the immobilized complex should be washed with an appropriate buffer after removal of the sample to ensure removal of substantially all unbound constituents.

The CD34$^+$ cells may then be released from the binding partner as described above, and collected by elution, filtration, centrifugation, precipitation or other appropriate means. The CD34$^+$ cells purified by the above method have the advantage of substantial yield and viability, which may be evaluated through the use of, for example, Trypan Blue or Propidium Iodide. The cells are also substantially free of noncellular components of the biological sample, as well as cells that do not express the CD34 surface antigen.

In yet another aspect of this invention, methods are provided for releasing a molecule that binds monoclonal antibody 12.8 (mAb12.8) from a complex that the molecule has formed with a binding partner. An example of such a molecule is the CD34 surface antigen. mAb12.8 is an IgM molecule that binds to CD34$^+$ cells, but not to peripheral blood lymphocytes, monocytes, granulocytes, platelets, red blood cells or thymocytes. The binding of mAb12.8 is dependent on the presence of sialic acid residues on the CD34 antigen, and its epitope is removed by glycoprotease treatment. The antibody may be prepared using the method of Andrews et al., *Blood* 67:842–45 (1986). Briefly, mAb12.8 may be raised against KG-1a cells, and monoclonal antibodies prepared by fusion of spleen cells with myeloma cells, using techniques well known to those of ordinary skill in the art. Hybrids that secrete antibody that binds to KG-1a cells, but not to peripheral blood granulocytes may then be identified and further screened for the binding properties discussed above. Such screens may be performed by any appropriate method known to those in the art, such as the methods described in Andrews et al., *Blood* 67:842–45 (1986), and Sutherland et al., *Stem Cells* 11(3):50–57 (1993), and references cited therein.

A molecule that binds to mAb12.8 may generally be released from a complex with a binding partner by contacting the complex with a carbohydrate containing a Neu5Acα2–3Gal moiety joined via a β1–4 linkage to a GlcNAc residue, or a structurally similar analog thereof, as discussed above. The amount of carbohydrate that should be contacted with the complex may be readily determined, as described above, and generally ranges from about 1 μg/mL to 50 mg/mL, typically 10 μg/mL to 10 mg/mL. The complex may be free or immobilized on a solid support, such as a chromatographic support, and the contacting may comprise passing the carbohydrate over a column containing immobilized complex or incubation. Released molecule may then by separated from the solution containing binding partner, as described above, by elution or other techniques known to those of ordinary skill in the art, including filtration, precipitation and centrifugation. As in the methods described above, the conditions under which the complex is contacted with carbohydrate should be similar to physiological conditions (e.g., near neutral pH with a buffer such as phosphate, Tris or HEPES in ionic conditions such as 0.15 M NaCl).

In yet another related aspect, this invention provides methods for purifying a molecule that binds to mAb12.8. Briefly, such purification may be achieved by contacting a solution containing such a molecule with a binding partner. The complex may then be separated from the remainder of the solution, and contacted with the carbohydrate to release the molecule from the complex with binding partner, as described above.

Suitable conditions for contacting the binding partner with the molecule are generally conditions that favor complex formation. Such conditions may be readily determined by one of ordinary skill in the art as described above, and include conditions similar to physiological conditions (e.g., near neutral pH with about 0.15 M NaCl). The amount of binding partner necessary to achieve adequate complexation of molecules that bind mAb12.8 will depend upon the concentration of such molecules, the binding constant for complex formation and the composition of the solution that contains the molecules. In general, an amount of binding partner ranging from about 0.1 μg/mL to 10 mg/mL, typically from about 1 μg/mL to 10 mg/mL, is sufficient.

Once complex formation is complete, the complex is separated from the remainder of the solution. This separation may be achieved using any of a variety of techniques, as described above. In general, an immobilized complex should be washed after removal of the sample to ensure substantial removal of all unbound components. The complexed molecule may then be released from the binding partner as described above, and collected by elution, filtration, centrifugation or precipitation, or other appropriate means.

In still another aspect of this invention, methods are provided for identifying compounds that bind to CD34$^+$ cells. Briefly, such methods comprise contacting a candidate compound with a carbohydrate as described above. Binding of carbohydrate to the candidate compound is then detected using any of a variety of means known to those of ordinary skill in the art. In this screen, candidate compounds that bind carbohydrate are identified as binding to CD34+ cells.

More specifically, a candidate compound may be contacted with a carbohydrate as described above, under conditions that promote complex formation. A candidate compound may be relatively pure, or may be present in an impure preparation, such as a hybridoma supernatant. In such screens, the candidate compound or the carbohydrate may be immobilized on a solid support, either before or after complex formation, as described above. The amount of carbohydrate used should be sufficient to permit detection of binding partners that have a binding constant for complex formation of $10^2$ L/mol or more.

Unbound solution components may then be removed from the immobilized complex by elution, filtration, precipitation, centrifugation or other appropriate means, and the solid support may be washed with an appropriate buffer, such as phosphate-buffered saline.

If the carbohydrate or candidate compound contains a reporter group, the presence of complexes may be detected directly. Preferred reporter groups include enzymes (such as horseradish peroxidase), substrates, cofactors, inhibitors, dyes, radionuclides, luminescent groups, fluorescent groups, constant immunoglobulin domains and biotin. Such groups may be incorporated into a carbohydrate or a candidate compound using chemical or recombinant means, which are well known to those of ordinary skill in the art.

Alternatively, a detection reagent may be added to the solid support after complex formation to detect the binding of carbohydrate to candidate compound. An appropriate detection reagent is any compound that binds to the immobilized complex, and that can be detected by any of a variety of means known to those in the art. For example, the detection reagent may contain a binding agent (e.g., an antibody or other molecule that specifically binds to the candidate compound) conjugated to a reporter group, as described above. In one preferred embodiment, the detection reagent comprises an antibody that binds to a carrier group on the carbohydrate (e.g., an anti-BSA antibody, which binds to a BSA carrier group). The conjugation of binding agent to reporter group may be achieved using standard methods known to those of ordinary skill in the art (see, e.g., catalog of Pierce Chemical Co., Rockford, Ill.). For example, radioactive iodine may be incorporated by generating an electrophilic iodine species ($I^+$) from sodium iodide. This allows the radioactive iodine to react with aromatic groups, such as tyrosine residues within the antibody. A fluorescent group may be incorporated into the binding agent using a variety of available fluorophores. For example, 7-amino-4-methylcoumarin-3-acetic acid (AMCA) (Pierce Chemical Co., Rockford, Ill.) attaches covalently to proteins by forming an amide bond between primary amines on the protein (e.g., lysine residues) and the N-hydroxysuccinimide group of the AMCA. Luminescent groups may be bioluminescent, such as luciferase, or chemiluminescent, such as acridinium ester.

In yet another assay format, a binding agent as described above without a reporter group may be allowed to bind to the complex, and then may be detected with a second, labeled detection reagent specific for the binding agent. For example, if the binding agent is an antibody, the detection reagent may be Protein A, Protein G, immunoglobulin, a lectin or free carbohydrate, coupled to a suitable reporter group as described above. Some common binding agents may be purchased conjugated to a variety of reporter groups from commercial sources (e.g., Zymed Laboratories, San Francisco, Calif., and Pierce, Rockford, Ill.). After incubation, the unbound detection reagent is removed prior to detection of the reporter group as described above.

In any format employing a detection reagent, the detection reagent is contacted with the immobilized complex for an amount of time sufficient to detect the bound compound. An appropriate amount of detection reagent and contact time may generally be determined from the manufacturer's instructions for the specific detection reagent or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Immunoglobulin reporter groups may be detected using Protein A. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

Alternatively, the immobilized complex may be detected by means that do not require the use of reporter groups or separation from unbound solution components. For example, where the support is a magnetic particle, the complex may be assayed by measuring the scattering of polarized light directed into the sample as the particles are moved within the sample by a magnetic field. This method of detecting bound complex is described, for example, in U.S. Pat. No. 4,725,140. If the support is a latex bead, the complex may be assayed based on the level of agglutination of the milky suspension of beads into clumps.

Where the support is a fiber optic sensor, the bound complex may be assayed by measuring a change in the sensor's detection of a solution property. In this embodiment, the sensor responds to the increase in the thickness of the reactive layer on the surface of the sensor resulting, for example, from the binding of candidate compound to a layer of immobilized carbohydrate. For example, if the sensor is capable of measuring refractive index, the bound candidate compound may be detected by measuring a shift in the refractive index detected by the sensor after incubation of the sensor with the compound. In samples containing a candidate compound that binds to the carbohydrate, more compound will bind to the immobilized carbohydrate, resulting in a thicker reactive layer and an increased shift in effective refractive index. Other principles of fiber optic detection such as evanescent wave and planar wave guides may also be employed.

Any of the above assays may also be performed as competitive assays. For example, carbohydrate and candidate compound may be combined and allowed to form a complex. The mixture may then be combined with a binding partner (e.g., antibody) specific for the carbohydrate. The antibody may have been immobilized on a suitable solid support prior to complex formulation, or may be immobilized after complex formation, as described above. Carbohydrate that has not bound to the candidate compound is then allowed to bind to the antibody, and the unbound carbohydrate and candidate compound is removed. The level of carbohydrate bound to the solid support, which may be determined using a reporter group by any of the methods described above, is inversely related to the level of antigen in the sample. Thus, a lower level of carbohydrate bound to the solid support indicates the presence of a candidate compound that binds to the carbohydrate.

Of course, other formats for assays to detect the binding of candidate compound to carbohydrate will be apparent to those of ordinary skill in the art, and the above formats are provided solely for exemplary purposes.

Antibodies for use as candidate compounds or as detection reagents in the above assays may generally be obtained using methods well known to those of ordinary skill in the art. For example, the technique of Kohler and Milstein, *Eur. J Immunol.* 6:511–519 (1976) and improvements thereto may be employed where monoclonal antibodies, rather than polyclonal antibodies, are desired. Briefly, these methods involve the preparation of immortal cell lines capable of producing antibodies having the desired specificity (i.e., reactivity with the carbohydrate of interest). Such cell lines may be produced, for example, from spleen cells obtained from an animal immunized with the carbohydrate immunogen. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. Alternatively, when the antibodies are to be used as candidate compounds in the above screening method, the hybridoma supernatants may be used with little or no purification.

The following Examples are offered by way of illustration and not by way of limitation.

EXAMPLES

Example 1

Preparation of Carbohydrates

This Example illustrates the preparation of representative carbohydrates for use in the methods of this invention.

A. 3'SL-APD-BSA

3'-sialyllactose (3'SL) may be coupled to serum albumin by way of aminophenylene diamine (APD) as follows.

The APD linker arm is derived from p-trifluoroacetamidoaniline (TFAN), which is synthesized from 4-trifluoroacetamidonitrobenzene. 2.76 g of p-nitroaniline is dissolved in 25 ml of redistilled pyridine, and the dark yellow solution is cooled in an ice bath. 5 ml of trifluoroacetic anhydride is added dropwise to the solution under constant stirring. The solution is then filtered on a sintered glass filter and washed with cold water. The solid material is recrystallized by adding approximately 100 ml of ethanol and gradually adding an additional 50 ml of ethanol while heating to 60° C. under stirring. The solution is covered and placed in the refrigerator overnight for recrystallization.

The solution is refiltered on a sintered glass filter, and the crystals are washed with cold water and dried under high vacuum. Yield of 4-trifluoroacetamidonitrobenzene is about 90–92% and the melting point is 140° C. The crystals are stored under desiccation at −20° C. or immediately subjected to reductive hydrogenation.

Reductive hydrogenation is achieved by adding 2 grams of 4-trifluoroacetamidonitrobenzene to 50 mg of palladium on activated charcoal in 30 ml of ethanol. Hydrogen gas is bubbled in the solution at room temperature for 3 hr. The solution is then filtered on Whatman No. 1 paper to remove the charcoal. The filter is washed with ethanol and the filtrate is pooled with the washing and evaporated to dryness by rotary evaporation. The product is crystallized by dissolving the residue in 20–40 ml of ethyl ether. Hexane is gradually added and the light pink crystals are collected by filtration and washed with hexane. The resulting 4-triluoroacetamidoaniline (TFAN) has a melting point of 118° C. and a yield of 76%.

TFAN is used to couple oligosaccharides such as 3'sialyllactose to amine-containing proteins such as serum albumin, as illustrated in FIG. 1. In the first step of the reaction, the oligosaccharide is coupled to TFAN by reductive amination followed by acetylation. 2 mg of 3'-sialyllactose is added to 10 mg of TFAN in 0.3 ml of ethanol/water 2:1 (v/v). 0.02 ml of glacial acetic acid and 6 mg of $NaCNBH_3$ is added under stirring. The glass vial is capped and incubated under stirring at 30° C. for 15–20 hr. The reaction is monitored by TLC, as described below.

0.05 ml of acetic anhydride is added and incubated at 30° C. for an additional 3 hr. The reaction is monitored for complete acetylation by TLC. The reaction is then transferred to a 13×100 mm glass test tube with a PTFE lined screw cap. 5 ml of ethyl acetate is added, followed by 5 ml of water for extraction. The phases are separated and the water phase is washed with another 5 ml of ethyl acetate. The water phases are combined and concentrated to 1–2 ml by rotary evaporation.

The concentrate is applied to a C18 column (4×0.4 mm i.d.) preconditioned with methanol followed by water. After washing with 5 column volumes of water, the N-acetylated TFAN derivative of 3'sialyllactose is eluted with 5 column volumes of methanol. The sample is evaporated to dryness by rotary evaporation.

The second step of the reaction removes the trifluoro group from the nitrogen. The dry TFAN derivative is dissolved in 0.5 ml of 0.5 M NaOH and incubated at room temperature for 3 h. The reaction is monitored by TLC.

The third step of the reaction converts the amine to an isothiocyanate. 1 ml of ethanol is added to the reaction, followed by 0.02 ml glacial acetic acid. The pH is adjusted to about 7 with 0.1 ml of 0.2 M NaOH. Under constant stirring, 0.004 ml of thiophosgen is carefully added. The pH is adjusted to above 5 with another 0.1 ml of 0.2 M NaOH. Conversion of the aromatic amine to the isothiocyanate is almost instantaneous.

The reaction product is extracted with 0.5 ml water and 1 ml ethyl ether. The upper phase (ether) is washed again with 0.5 ml water. The water phases are combined and rotary evaporated to 0.5–1 ml.

The last step of the reaction couples the isothiocyanate derivative to the amine-containing carrier molecule, such as serum albumin. The isothiocyanate derivative is transferred to a 5 ml vial containing 5 mg of bovine serum albumin in 0.1 M borate buffer at pH 9.4. The pH of the solution is readjusted to pH 9.4 with 0.5 M NaOH. The reaction is incubated under constant stirring at room temperature for at least 20 hr, and is monitored by TLC. The reaction is then dialyzed against three changes of 20 mM $NH_4HCO_3$, lyophilized and the degree of coupling is characterized using standard assays for protein and sialic acid.

The TLC analyses described above are performed on silica gel 60 HPTLC thin layer plates in ethyl acetate/ methanol/acetic acid/water, 6:3:3:2 (v/v/v/v). The Rf values are as follows:

| Compound | Rf Value |
| --- | --- |
| 3'SL | 0.22 |
| 3'SL-TAD | 0.43 |
| 3'SL-NAc-TAD | 0.39 |
| TAD | 1.00 |
| 3'SL-NAc-aniline | 0.08 |
| 3'SL-NAc—Ph—N=C=S | 0.66 |

B. 3'SL-APEA-BSA

APEA is coupled to 3'-sialyllactose by reductive amination. 5 mg of $NaBH_4$ and 2 mg of 3'sialyllactose are added to 0.25 ml APEA and incubated under stirring for 16 hr at 35° C. Excess reagent is destroyed by adding acetic acid to lower the pH to 5.6 in an ice bath. The sample is evaporated to dryness by rotary evaporation.

The sample is dissolved in 0.1 M pyridine/acetate buffer, pH 5.0 and chromatographed in the same buffer on BioGel P-2. The fractions that are both UV adsorbent and orcinol positive are combined and evaporated to dryness. The sample is dissolved in water and passed through a C18 column. The product (3'sialyllactose-APEA) is not retained by the column and is collected.

0.73 mg of 3'-sialyllactose-APEA is added to 0.2 ml of 0.5 M NaAc and 0.4 ml ethanol. While stirring carefully, 1.6 μl of thiophosgen is added. Neutral pH is maintained by the addition of 0.2 M NaOH. After 10 min., the mixture is evaporated to near dryness and reconstituted with 0.8 ml of 0.1 M borate buffer, pH 9.5. Synthesis of the isothiocyanate derivative is monitored by TLC as described below.

0.2 mg of serum albumin is added directly to the 3'-sialyllactose-APEA-isothiocyanate derivative. The reaction is incubated at room temperature under constant stirring for 48 hr and monitored by TLC. The 3'-sialyllactose-albumin containing solution is then dialyzed against an appropriate buffer.

The TLC analyses are performed as described above, with the following Rf values:

| Compound | Rf Value |
| --- | --- |
| 3'SL | 0.22 |
| 3'SL-APEA | 0.057 |
| 3'SL-APEA-isothiocyanate | 0.55 |
| 3'SL-APEA-albumin | 0.00 |

C. Neu5Acα2–3(Galβ1–4GlcNAcβ1–3)$_n$

This polylactosamine derivative, wherein n is an integer from 1 to 50, is prepared by a chemical disaccharide polymerization to form polylactosamine oligomers, followed by the enzymatic addition of sialic acid to the terminal galactose residue to form sialylated polylactosamine.

Figure 3:
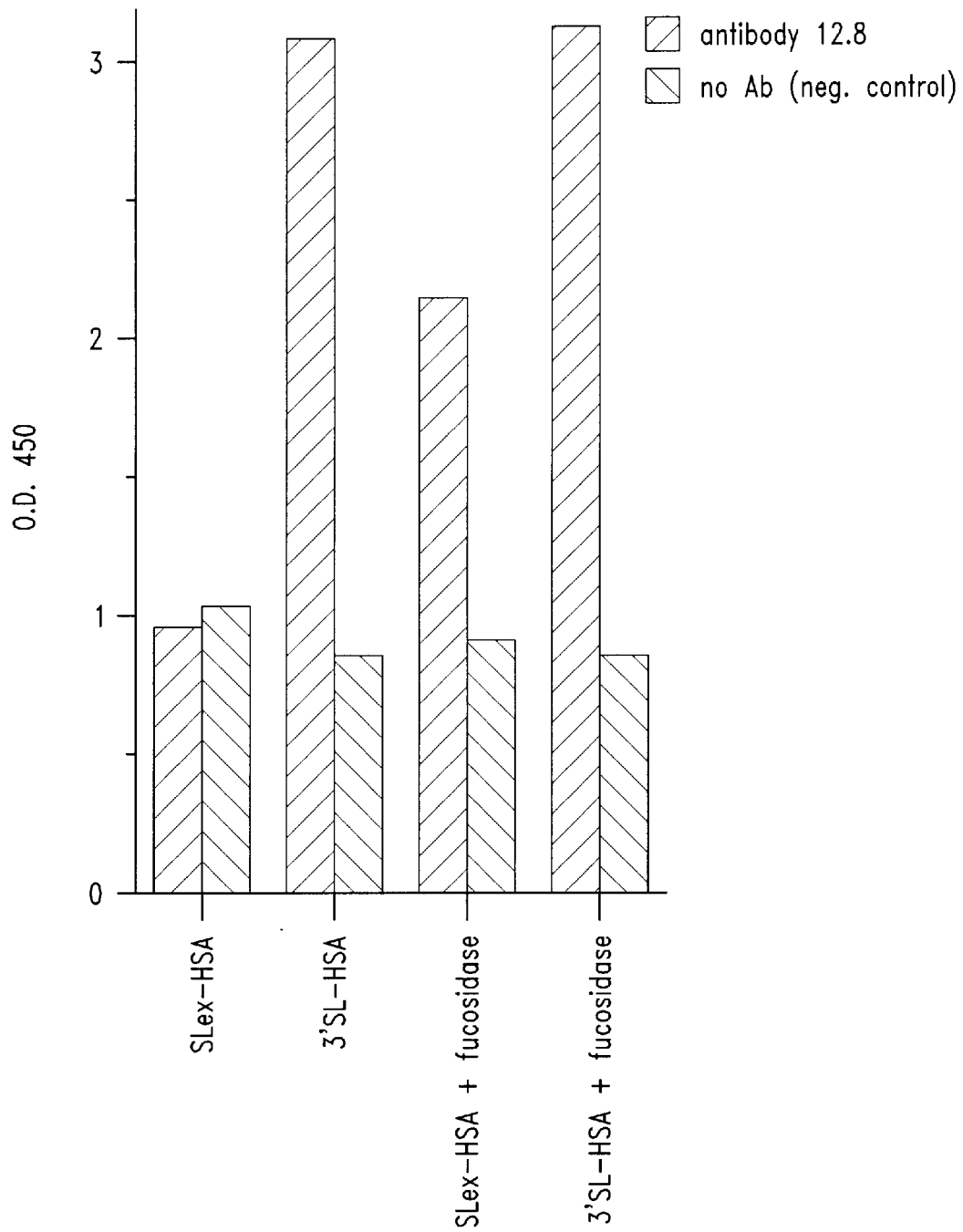
FIG. 3 shows the effect of fucosidase treatment on the binding of the SLe$^x$ carbohydrate epitope to mAb12.8.

The protected disaccharide required for the polymerization reactions is prepared by the condensation of two blocked sugars, followed by polymerization by reaction with dichloromethane in methyl triflate, according to the procedure of Srivastava et al., *J. Carbohydrate Chem.* 10:927–933 (1991). The resulting blocked disaccharide is as shown in FIG. 3. After 24 hours, pentamers of the polymerization are recovered, and longer incubation times result in increasing lengths.

The sialic acid is added to the terminal galactose residue according to the procedure of De Vries et al., Biochem. 33:9937–9944 (1994).

D. 3'SL-APD-dendrimer

3'-sialyllactose is conjugated to a generation 4 starburst dendrimer via APD as described in part A above except that, in the last step, dendrimer (Aldrich Chemical Co., Milwaukee, Wis.) is substituted for the bovine serum albumin. The amount of dendrimer depends on the desired mole ratio of 3'SL to dendrimer. To prepare a glycoconjugate having a 15:1 mole ratio, the molar amount of dendrimer is ¹⁄₁₅th of the molar amount of 3'SL.

E. 3'SL-APEA-dendrimer

3'-sialyllactose is conjugated to a generation 4 starburst dendrimer via APEA as described in part B above, except that the serum albumin is replaced by an amount of dendrimer sufficient to result in the desired molar ratio of 3'SL to dendrimer.

Example 2

Carbohydrate Binding to mAb12.8

This Example illustrates the binding of the carbohydrates 3'SL-HSA and Neu5Acα2–3Galβ1–4GlcNAcβ1–3Galβ1–4 (Glc)-HSA to mAb12.8.

A. Binding of 3'SL-HSA to mAb12.8

The binding of 3'SL-HSA to mAb12.8 is demonstrated using an enzyme-linked immunosorbent assay (ELISA). Microtiter plates are prepared with serial dilutions of 3'SL-HSA (prepared as described in Example 1) in Tris-$Ca^{++}$ buffer (0.05M Tris HCl, pH 7.5, 0.15 M NaCl, 2 mM $CaCl_2$), starting with 500 ng/well. The plates are incubated at 37° C. for 1 hour to immobilize the carbohydrate on the plastic well surface.

100 μl of 2% BSA in Tris-$Ca^{++}$ buffer is added to each well, and the plates are incubated at room temperature for 1 hour, and washed 3 times with Tris-$Ca^{++}$ buffer. 100 μl of 10 μg/mL mAb12.8 in 1% BSA Tris-$Ca^{++}$ buffer is then added to each well, and the plates are incubated at room temperature for 2 hours. Again, the plates are washed 3 times with Tris-$Ca^{++}$ buffer.

100 μl of 1 μg/mL peroxidase-labeled goat anti-mouse IgM (KPL, Inc., Gaithersburg, Md.) in 1% BSA Tris-$Ca^{++}$ buffer is added to each well, and the plates are incubated at room temperature for 1 hour, and washed 3 times with Tris-$Ca^{++}$ buffer. 100 μl of TMB (tetramethylbenzidine) substrate solution (KPL, Inc., Gaithersburg, Md.) is then added to each well, and the reaction is allowed to proceed for 2 minutes. The reaction is stopped, and detection enhanced, by the addition of 100 μl of 1M formic acid/well. The absorbance at 450 nm is then determined in a Titertek Multiskan MCC/340 plate reader (Flow Laboratories, Inc., McLean, Va.).

At amounts of 3'SL-HSA less than about 70 ng/well, the A450 is approximately 0.5. However, at about 100 ng 3'SL-HSA per well, the A450 increases to greater than 1, and approaches 3 at about 200 ng per well. This indicates that 3'SL-HSA binds to mAb12.8.

B. Effect of Varying Linker Arm and Carrier Group on Carbohydrate Binding to mAb12.8

The effect of altering the chemical linker arm and carrier group on the 3'SL binding to mAb12.8 is evaluated using the following carbohydrates, prepared as described in example 1: 3'SL-APD-dendrimer, 3'SL-APD-BSA, 3'SL-APEA-BSA, 3'SL-APD-HSA and 6'SL-APD-HSA.

100 μl of each of the above carbohydrates is added to duplicate wells in a 96-well microtiter plate at 0.5 μg/ml. The plates are incubated overnight at 4° C. to immobilize the carbohydrates on the plastic well surface. The wells are then washed three times and filled with Tris-Ca$^{++}$ buffer (0.05 M Tris-HCl, pH 7.5, 0.15 M NaCl, 2 mM CaCl$_2$) containing 1% BSA. The plates are then incubated for 1 hour at room temperature to block nonspecific binding.

The plates are washed three times with Tris-Ca$^{++}$ buffer and mAb 12.8 (100 μl of 10 μg/ml in Tris-Ca$^{++}$ buffer) is added to all wells except one negative control for each condition. The plates are incubated for an additional two hours at room temperature.

The plates are again washed three times with Tris-Ca$^{++}$ buffer and peroxidase-labeled goat anti-mouse IgM (100 μl of 1 μg/ml in Tris-Ca$^{++}$ buffer) is added to all wells. The plates are incubated for 1 hour at room temperature.

Wells are washed five times with Tris-Ca$^{++}$ buffer and 100 μl of tetramethylbenzidine solution (TMB substrate solution, KPL, Inc., Gaithersburg, Md.) is added. Color is allowed to develop for two minutes, and the reaction is stopped (and detection enhanced) by the addition of 100 μl of 1 M formic acid. The microtiter plate is read in a Titertek Multiskan MCC/340 plate reader (Flow Laboratories, Inc., McLean, Va.) set at a wavelength of 450 nm.

Figure 2:
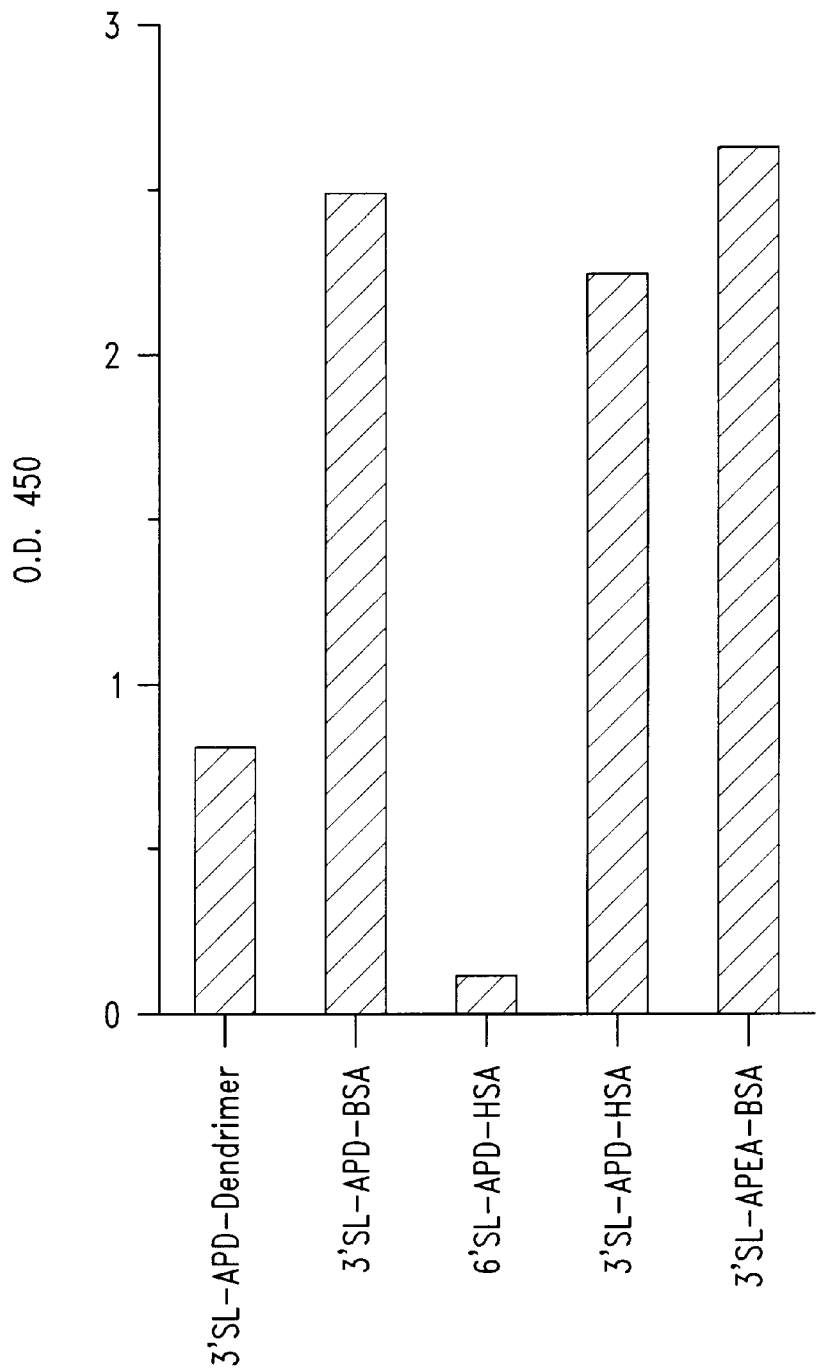
FIG. 2 illustrates the binding of representative carbohydrates of this invention to mAb12.8, relative to a control carbohydrate.

The results, shown in FIG. 2, demonstrate that mAb12.8 binds to all of the carbohydrates containing 3'-sialyllactose regardless of the linker arm (e.g., APD or APEA) or the carrier (BSA, HSA or dendrimer). In contrast, a carbohydrate containing 6'-sialyllactose (6'-SL-HSA) does not bind mAb12.8. The lower reactivity of the dendrimer in this experiment is probably due to its relative inability to immobilize in the plastic wells compared to the albumin (HSA and BSA) conjugates.

C. Binding of Defucosylated SLe$^x$ Epitope to mAb12.8

In a related experiment, the binding of a partially defucosylated SLe$^x$ epitope (coupled to HSA) is evaluated using a similar ELISA. 250 ng of SLe$^x$-HSA (or, as a positive control, 3'SL-HSA) in 100 μl of Tris-Ca$^{++}$ buffer is immobilized on microtiter wells by incubating for 1 hour at 37° C. 100 μl of 2% BSA in Tris-Ca$^{++}$ buffer is added to each well to block further non-specific binding, and the plates are incubated at room temperature for 1 hour, followed by 2 washes with Tris-Ca$^{++}$ buffer. 200 units per well of α1–3,4 fucosidase (New England Biolabs, Beverly, Mass.) in citrate buffer (pH 4.0) is then added to half of the wells. The plates are covered and incubated at 37° C. overnight.

The plates are then washed three times with Tris-Ca$^{++}$ buffer and mAb12.8 (100 μl of 10 μg/mL mAb12.8 in Tris-Ca$^{++}$ buffer) is then added to each well except for 1 negative control for each condition. The plates are incubated at room temperature for 2 hours.

The plates are then washed 3 times with Tris-Ca$^{++}$ buffer, and 100 μl of 1 μg/mL peroxidase-labeled goat anti-mouse IgM (KPL, Inc., Gaithersburg, Md.) in 1% BSA Tris-Ca$^{++}$ buffer is added to each well. The plates are incubated at room temperature for 1 hour. The wells are then washed 5 times with Tris-Ca$^{++}$ buffer, and 100 μl of TMB substrate solution (KPL, Gaithersburg, Md.) is added to each well, and the reaction is allowed to proceed for 2 minutes. The reaction is stopped, and detection enhanced, by the addition of 100 μl of 1M formic acid/well. The absorbance at 450 nm is then determined in a Titertek Multiskan MCC/340 plate reader (Flow Laboratories, Inc., McLean, Va.).

The results are presented in FIG. 3. In the absence of fucosidase treatment, 3'SL-HSA, but not SLe$^x$-HSA, binds to mAb12.8. Fucosidase treatment of 3'SL-HSA had no detectable effect on binding of mAb12.8. However, fucosidase treatment of SLe$^x$-HSA, which results in partial removal of the fucose residues, significantly increases the level of binding of that carbohydrate to mAb12.8.

These results indicate that 3'SL-HSA and Neu5Acα2–3Galβ1–4GlcNAc β1–3Galβ1–4(Glc)-HSA bind to mAb12.8. Since Neu5Acα2–3Galβ1–4GlcNAcβ1–3Gal β1–4(Glc)-HSA contains a monomer of sialylpolylactosamine, these results also indicate that longer polymers of sialylpolylactosamine will bind mAb12.8.

Example 3

Characterization of mAb12.8 Epitope

To illustrate the specificity of the interaction between 3'SL-HSA and mAb12.8, and to further characterize the epitope of the antibody, the assay described in Example 2, part A, is performed using the control carbohydrates shown below:

```
6'SL-HSA:  Neu5Acα2-6Galβ1-4(Glc)-APD-HSA
LSTa-HSA:
Neu5Acα2-3Galβ1-3GlcNAcβ1-3Galβ1-4(Glc)-APD-HSA
SLe^x-HSA:
Neu5Acα2-3Galβ1-4GlcNacβ1-3Galβ1-4(Glc)-APD-HSA
                      3
                      |
                      Fucα1
GM_3:      Neu5Acα2-3Galβ1-4Glcβ1-1Ceramide
```

These control carbohydrates are selected because of their structural similarity to 3'SL-HSA, and may be obtained from commercial sources such as Oxford GlycoSystems, Rosedale, N.Y.

The assays of each of the above HSA conjugates are performed as described for 3'SL-HSA. For GM$_3$, the assay is as described above except that dilutions of GM$_3$ are prepared in methanol, and immobilization on the plastic well surface is achieved by allowing the methanol to completely evaporate under an exhaust hood. After immobilization, 100 μl of 1% BSA in Tris-Ca$^{++}$ buffer is added to the wells containing GM$_3$.

Figure 4:
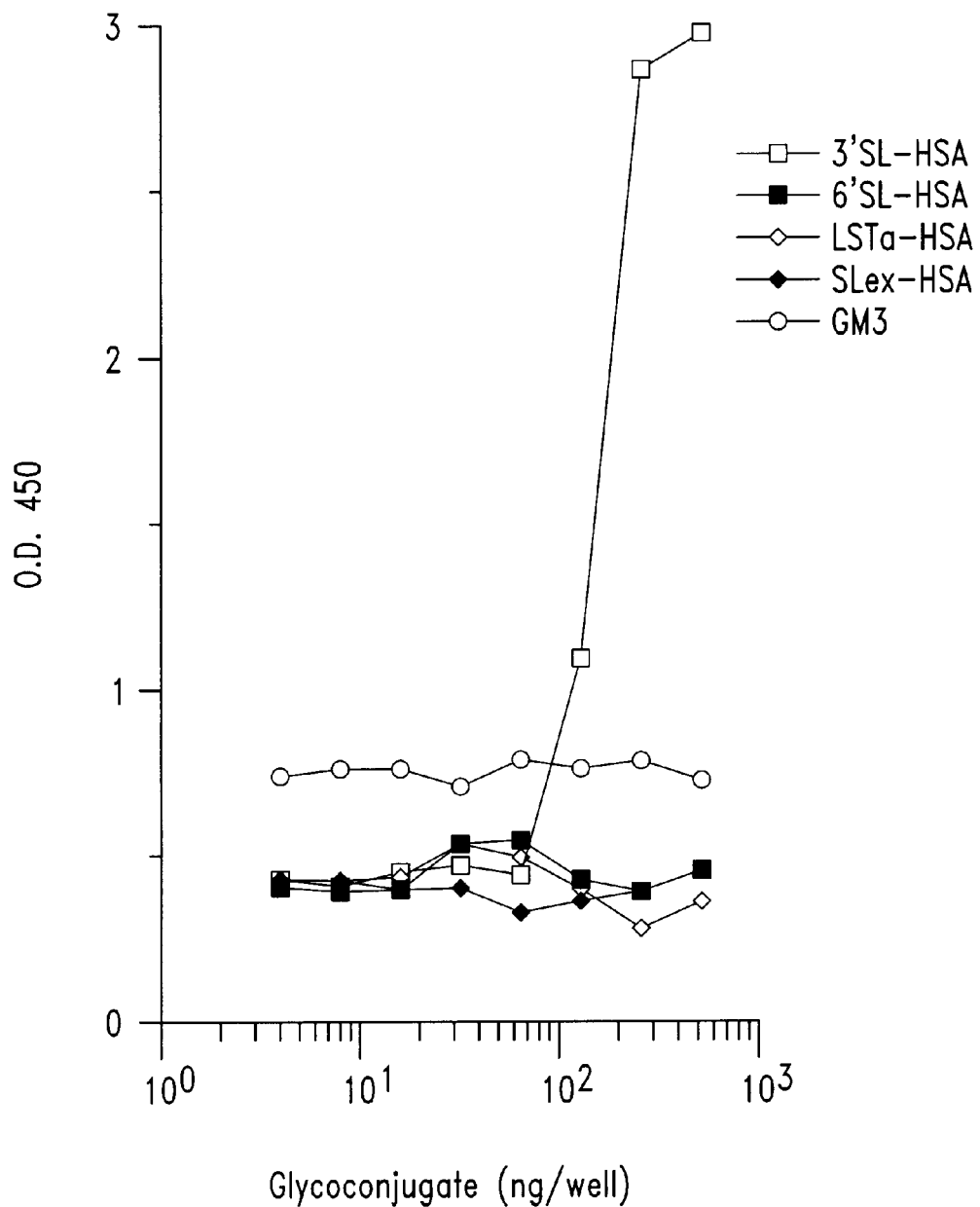
FIG. 4 illustrates the binding of a representative carbohydrate of this invention to mAb12.8, relative to the binding observed for several control carbohydrates.

No binding of any of the control carbohydrates to mAb12.8 is detected in these assays. As shown in FIG. 4, which compares the A450 for 3'SL with that of the control carbohydrates, only 3'SL-HSA binds mAb12.8.

This experiment further characterizes the mAb12.8 epitope. For example, the experiment shows that in 3'SL-HSA, the opened ring configuration for glucose (which mimics the three dimensional structure of GlcNAc) is required for binding. mAb12.8 does not bind the naturally-occurring ganglioside GM$_3$ (i.e., 3'SL coupled to ceramide), in which the glucose ring is in the closed configuration. However, when 3'SL is coupled to HSA or BSA, using APD or APEA, the glucose ring is opened and coupled to the spacer arm by reductive amination. mAb12.8 also binds 3'SL coupled, via APD, to a dendrimer (not shown).

In addition, the α2–3 linked sialic acid is necessary for mAb12.8 binding. mAb12.8 does not bind 6'SL-HSA, which is identical to 3'SL-HSA except for the α2–6 linkage of the sialic acid. mAb12.8 also does not bind SLe$^x$-HSA, which contains a fucose residue linked to the GlcNAc residue. Finally, mAb12.8 does not bind LSTa-HSA, which shows that the binding requires type 2 chains (e.g., . . . Galβ1–4GlcNAc . . . ), and that the antibody does not recognize type 1 chains (e.g., . . . Galβ1–3GlcNAc . . . ).

Example 4

Inhibition of CD34⁺-Cell Binding to mAb12.8 by 3'SL-HSA

This Example illustrates the use of a representative carbohydrate according to this invention to release KG1A cells (ATCC No. CCL246.1, Rockville, Md.) bound to mAb12.8.

Monoclonal antibody 12.8 is immobilized on 35 mm tissue culture dishes by adsorption, as shown below:

| Dish | Substrate 1 | Substrate 2 |
|---|---|---|
| 1 | none | none |
| 2 | 12.8 (250 ng) | BSA (2%) |
| 3 | 12.8 (250 ng) | BSA (2%) |

Each substrate is coated on the dish and incubated at 37° C. for 1 hour prior to adding the next substrate or running the flow assay. The flow assay utilizes a parallel plate flow chamber mounted on an inverted-stage microscope to visualize the adhesive interactions between cells and substrates. Each dish is attached to the flow chamber and mounted on the microscope stage.

Figure 5:
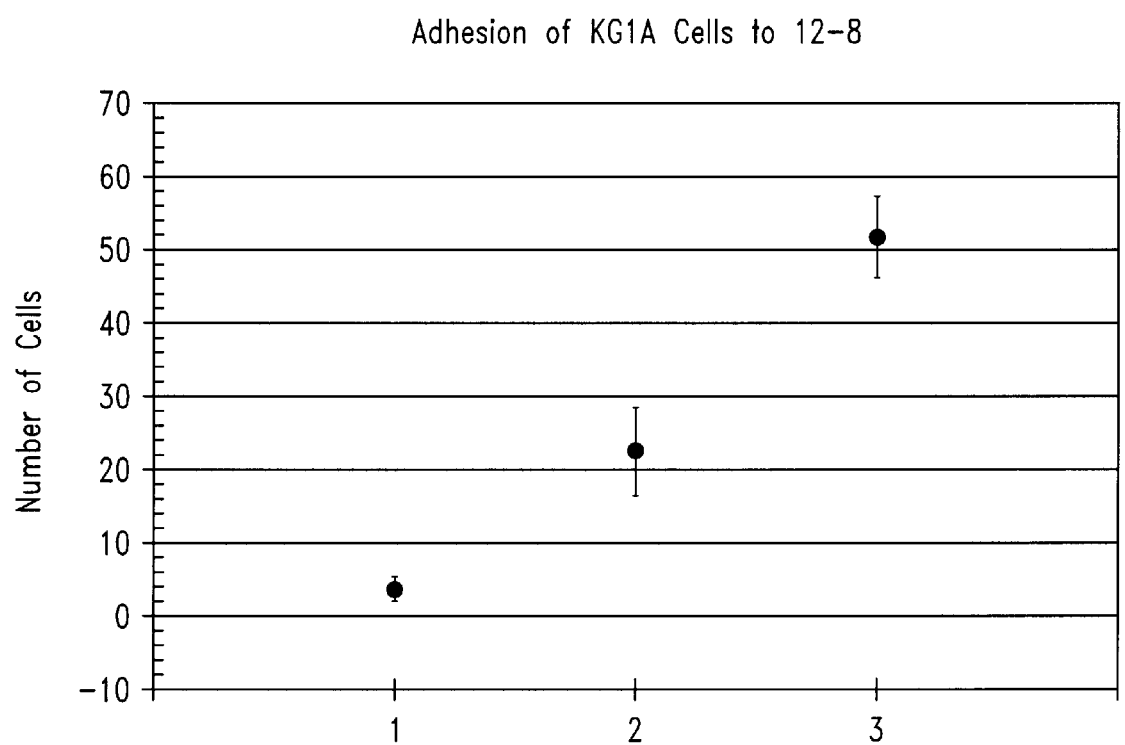
FIG. 5 illustrates the use of a representative carbohydrate of this invention to inhibit the binding of CD34$^+$ cells to mAb12.8.

To prevent binding of the cells to mAb12.8 by way of Fc receptors on the cell surface, human IgG (200 $\mu$g/mL) is added to the KG1A cells 10 minutes prior to the flow assay. In addition, 200 ng of 3'SL-HSA is added to dish 2, and 200 ng of 6'SL-HSA is added to dish 3, and flow is initiated such that the cells flow over the surface of the dish at a wall shear stress of 0.48 dynes/cm$^2$ for 2 minutes, prior to collecting images at 7 different locations on the dish. The images are then quantified, using video microscopy coupled to digital image processing, to determine the number of adherent cells in each image, and the number of cells in the 7 images are averaged. These averages, along with the 98% confidence limits, are shown in FIG. 5.

These results indicate that 3'SL-HSA, but not 6'SL-HSA, inhibits the binding of KG1A cells to mAb12.8.

Example 5

Purification of CD34⁺-Cells

This example illustrates the purification of CD34⁺ cells from umbilical cord blood.

10 ml of cord blood is mixed with 26 ml of Ca$^{++}$ and Mg$^{++}$ free PBS. 4 ml of 10% Dextran (M.W. 200,000–300,000) in PBS is then added and the cells are allowed to settle for 25 minutes. The supernatant is then removed. 36 ml PBS is then added, followed by 4 ml of 10% Dextran. The solution is mixed and allowed to settle for 45 minutes. The supernatant is removed and the supernatants are combined. The cells are centrifuged and washed twice with 1% BSA in PBS. The sample is resuspended to 1–2×10$^8$ cells/ml in 1% BSA.

The CD34⁺ cells are immobilized on a CEPRATE LC34-2 avidin column (CellPro, Inc., Bothell, Wash.) according to the manufacturer's instructions. Following removal of unadsorbed (non-target) cells according to the manufacturer's instructions, the CD34⁺ cells are eluted from the column as follows:

4 ml of PBS containing an elution carbohydrate (5 mg/ml) is added to the wash chamber. The outlet is opened and 3 ml is collected. The outlet is then closed for 45 minutes. After opening the outlet, 1 ml remaining in the wash chamber is allowed to enter the avidin column while collecting cells. 4 ml of PBS is then added to the wash column and the entire volume is collected to recover the maximum number of cells.

The eluted cells may be counted using a hemacytometer or automated cell counter. Cell viability is determined by Trypan Blue exclusion.

Example 6

Identification of Compounds that Bind CD34⁺-Cells

This example illustrates the identification of compounds capable of binding CD34⁺ cells, using a latex bead agglutination assay or a biosensor assay.

A. Latex Bead Agglutination Assay

Sialylpolylactosamine is chemically linked to amine-containing latex microparticles (Polybead™, Catalog No. 07763, 0.5 $\mu$m diameter, Polysciences, Inc., Warrington, Pa.) using the APD linker, as described in Example 1. 10 $\mu$l of a 1.25% dispersion of ligand-conjugated beads is added to 50 $\mu$l of test extract in 10 mM HEPES pH 7.3, 150 mM NaCl (HBS) containing 2 mM CaCl$_2$, MgCl$_2$, MnCl$_2$ and ZnCl$_2$ in the wells of a 96-well microtiter plate, and the plate is covered. The plate is rotated at room temperature for 1 hour. Binding partner is detected by agglutination or clumping of beads either visually or by measuring a decrease in light scattering (increase of signal) in a Titertek Multiskan MCC/340 plate reader (Flow Laboratories, Inc., McLean, Va.) set at a wavelength of 690 nm. mAb12.8 is employed as a positive control test compound.

B. Biosensor Assay

A commercially available biosensor, BIA Core™ (Pharmacia Biosensor AB) is used to rapidly assay unlabeled mixtures of proteins for binding partners to the immobilized carbohydrate ligands. The sensor in this instrument measures binding interactions by surface plasmon resonance. A thin film of gold coated with carboxymethylated dextran (CMD) covers the glass plate of the sensor surface, and appropriate ligands are immobilized on the surface through the CMD layer. A prism on the sensor surface detects changes in the refractive index which correlate with the surface plasmon resonance response of a binding partner.

To detect binding partners for CD34⁺ cells, the polylactosamine derivative of 3'SL, prepared as described Example 1, may be employed. The sensor is equilibrated by washing with 10 mM HEPES pH 7.3, 150 mM NaCl, 0.05% (v/v) surfactant P-20 (HBS). The instrument is injected with 35 $\mu$l of a 1:1 (v/v) mixture of 0.1 M N-hydroxysuccinimide (NHS) and 0.1 M N-ethyl-N'-(dimethylaminopropyl) carbodiimide for a pulse of 7 minutes. A 7-minute pulse containing 35 $\mu$l of 100 $\mu$g APD-sialylpolylactosamine/ml is injected in 10 mM sodium acetate, pH 4.0, to immobilize the ligand on the biosensor surface. Unreacted NHS esters are blocked by a subsequent 7-minute injection of 35 $\mu$l of 1 M ethanolamine, pH 8.5.

The sensor is washed with three, 3-minute pulses of 0.1 M glycine-HCl pH 3.0 and is equilibrated in HBS. Extracts are tested for binding partners by injecting a 2-minute pulse of test material at a minimum of 20 $\mu$g/ml in HBS containing 2 mM each of CaCl$_2$, MgCl$_2$, MnCl$_2$, and ZnCl$_2$. Binding partner is detected by determining a change over the baseline signal which is measured 140 seconds after the start of the injection in order to control for any possible effects due to buffer changes. mAb12.8 is employed as a positive control for obtaining a surface plasmon resonance response.

From the foregoing, it will be appreciated that, although specific embodiments of the invention have been described herein for the purpose of illustration, various modifications may be made without deviating from the spirit and scope of the invention.

I claim:

1. A method for screening for a candidate compound able to bind to CD34⁺ cells, comprising the steps of:
   (a) contacting a candidate compound with an isolated carbohydrate having the structure:

Neu5Acα2–3Galβ1–4(X)

wherein (X) is GlcNAc, or a monosaccharide or a cyclohexane derivative that is structurally similar to GlcNAc; and
   (b) detecting candidate compound bound to said carbohydrate, thereby identifying a candidate compound that binds to CD34⁺ cells.

2. The method of claim 1, wherein said carbohydrate has the structure:

Neu5Acα2–3(Galβ1–4GlcNAcβ1–3)$_n$ wherein n is an integer from 1 to 50.

3. The method of claim 1, wherein said carbohydrate is immobilized on a solid support.

4. The method of claim 3, wherein said solid support comprises glass, latex, nitrocellulose, a magnetic particle, polyacrylamide, agarose, dextran or a plastic material.

5. The method of claim 1 wherein said carbohydrate includes a carrier group.

6. The method of claim 5 wherein said carrier group is selected from the group consisting of albumin, polylysine, polyamidoamines, peptides, immunogenic proteins, polystyrene, polyacrylamide, lipids, ceramide, and dendrimers.

7. A method for screening for a candidate compound able to bind to CD34⁺ cells, comprising the steps of:
   (a) contacting a candidate compound with an isolated carbohydrate having the structure:

Neu5Acα2–3Galβ1–4(X)

wherein (X) is GlcNAc, or a monosaccharide or a cyclohexane derivative that is structurally similar to GlcNAc, and wherein said carbohydrate is immobilized on a solid support;
   (b) contacting said immobilized carbohydrate with a binding partner for said carbohydrate;
   (c) separating unbound binding partner from said immobilized carbohydrate; and
   (d) detecting binding partner bound to said immobilized carbohydrate, thereby identifying a candidate compound that binds to CD34⁺ cells.

8. The method of claim 7, wherein said binding partner is monoclonal antibody 12.8.

9. The method of claim 7, wherein said step of detecting binding partner bound to said immobilized carbohydrate comprises contacting said binding partner with a detection reagent, wherein said detection reagent contains a reporter group.

10. The method of claim 9, wherein said reporter group is selected from the group consisting of radioisotopes, luminescent groups, fluorescent groups, enzymes, and dyes.

* * * * *